(12) United States Patent
Thomas et al.

(10) Patent No.: US 10,434,206 B2
(45) Date of Patent: Oct. 8, 2019

(54) CLOSURE ELEMENT FOR A MEDICAL STERILE CONTAINER, AND STERILE CONTAINER WITH SUCH A CLOSURE ELEMENT

(71) Applicant: Aesculap AG, Tuttlingen (DE)

(72) Inventors: Stefan Thomas, Tuttlingen (DE); Serkan Bellikli, Tuttlingen (DE); Matthias Schweizer, Tuttlingen (DE); Stefan Schuster, Villingen-Schwenningen (DE); Dieter Weisshaupt, Immendingen (DE)

(73) Assignee: Aesculap AG (DE)

( * ) Notice: Subject to any disclaimer, the term of this patent is extended or adjusted under 35 U.S.C. 154(b) by 102 days.

(21) Appl. No.: 15/529,176

(22) PCT Filed: Nov. 27, 2015

(86) PCT No.: PCT/EP2015/077956
§ 371 (c)(1),
(2) Date: May 24, 2017

(87) PCT Pub. No.: WO2016/083595
PCT Pub. Date: Jun. 2, 2016

(65) Prior Publication Data
US 2017/0360976 A1    Dec. 21, 2017

(30) Foreign Application Priority Data
Nov. 28, 2014 (DE) .................. 10 2014 117 516

(51) Int. Cl.
*A61L 2/00* (2006.01)
*A61L 2/26* (2006.01)
*A61B 50/00* (2016.01)

(52) U.S. Cl.
CPC .......... *A61L 2/26* (2013.01); *A61B 2050/0074* (2016.02); *A61L 2202/182* (2013.01); *A61L 2202/24* (2013.01)

(58) Field of Classification Search
CPC ................ A61L 2/26; A61B 2050/006; A61B 2050/0067; A61B 2050/0086
(Continued)

(56) References Cited

U.S. PATENT DOCUMENTS

| 4,915,913 A | 4/1990 | Williams et al. |
| 5,725,830 A | 3/1998 | Taschner |

(Continued)

FOREIGN PATENT DOCUMENTS

| CN | 104169998 A | 11/2014 |
| DE | 3116036 A1 | 11/1982 |

(Continued)

OTHER PUBLICATIONS

European Patent Office English Translation of the Description and the Claims sections of DE-102004028040-A1.*

(Continued)

*Primary Examiner* — Monzer R Chorbaji
(74) *Attorney, Agent, or Firm* — RatnerPrestia (57) ABSTRACT

A closure for a medical sterile container having a trough-like first container part and a lid-type second container part includes a closure flap which can be arranged on one of the container parts so as to be able to pivot between a closed position, in which the container parts are interlocked with each other by the closure, and an open position in which the container parts are unlocked. The closure includes a latch element which in the closed position of the closure interlocks the closure flap with the other container part.

17 Claims, 7 Drawing Sheets

(58) Field of Classification Search
USPC .................................. 422/50, 300; 220/200
See application file for complete search history.

(56) References Cited

U.S. PATENT DOCUMENTS

| | | |
|---|---|---|
| 10,329,060 B2 | 6/2019 | Weisshaupt et al. |
| 2015/0014315 A1 | 1/2015 | Weisshaupt et al. |
| 2015/0225136 A1 | 8/2015 | Weisshaupt et al. |

FOREIGN PATENT DOCUMENTS

| | | | | |
|---|---|---|---|---|
| DE | 3316141 A1 | 11/1984 | | |
| DE | 9007070 U1 | 9/1990 | | |
| DE | 9203630 U1 | 6/1992 | | |
| DE | 4411970 A1 | 10/1995 | | |
| DE | 29907481 U1 | 8/1999 | | |
| DE | 102004028040 A1 * | 10/2005 | ............... | A61L 2/26 |
| DE | 102004028040 A1 | 10/2005 | | |
| DE | 202012002487 U1 | 5/2012 | | |
| EP | 1857375 A1 | 11/2007 | | |
| WO | 9201480 A1 | 2/1992 | | |
| WO | 2013135658 A1 | 9/2013 | | |
| WO | 2014029587 A1 | 2/2014 | | |

OTHER PUBLICATIONS

International Search Report with partial English language translation for International Application No. PCT/EP2015/077956, dated Feb. 23, 2016, 16 pages.
German Search Report with English language translation for Application No. 10 2014 117 516.6, dated Jul. 1, 2015, 14 pages.
Chinese Office Action for Chinese Application No. 201580074936.1, dated May 29, 2019, with translation, 10 pages.

* cited by examiner

CLOSURE ELEMENT FOR A MEDICAL STERILE CONTAINER, AND STERILE CONTAINER WITH SUCH A CLOSURE ELEMENT

RELATED APPLICATIONS

This application is the United States national phase entry of International Application No. PCT/EP2015/077956, filed Nov. 27, 2015, which is related to and claims the benefit of priority of German Application No. DE 10 2014 117 516.6, filed Nov. 28, 2014. The contents of International Application No. PCT/EP2015/077956 and German Application No. DE 10 2014 117 516.6 are incorporated by reference herein in their entireties.

FIELD

The present invention relates to a closure for a medical sterile container comprising a trough-like first container part and a lid-type second container part, comprising a closure flap which can be arranged on one of the container parts so as to be able to pivot between a closed position, in which the container parts are interlocked with each other by means of the closure, and an open position in which the container parts are unlocked, as well as to a medical sterile container comprising a closure of this type.

BACKGROUND

Sterile containers comprising such a closure are used in the medical field, in particular in surgery, in order to sterilize surgical instruments, implants and the like and to store and transport them for a short term after sterilization. Objects to be sterilized are arranged in the container interior. The container is closed by arranging the container lid on the lower container part and together with the objects to be sterilized and received therein is transported to a sterilizer in which the container interior is acted upon with a sterilizing gas such as water vapor, for instance. In order to avoid any recontamination after sterilization and to be able to ensure the sterility of the objects received in the container, it is known to provide containers with a seal when the sterilization has been completed.

From DE 92 03 630 U1, a clamping fastener for surgical sterilization containers and other receptacles is known, which comprises a closure lug that can be pivoted from an open into a closed position and vice versa, and in its closed position connects a preferably trough-shaped, first container part to a second container part formed as a lid, wherein the clamping fastener is implemented as a toggle lever type closure or eccentric closure whose closure lug comprises a clamping lug part which is pivotally arranged on the one container part and on which a traction lug part is pivotally supported at a distance to the pivot axis, which traction lug part in the closed position of the clamping fastener engages behind a closure hook provided on the other container part, wherein the traction lug part on its side facing the closure hook comprises a lug protrusion or similar edge portion angled inwardly which in the closed position overlaps or engages behind the closure hook.

From DE 31 16 036 C2, a sterilization container is known which comprises a lid that can be held in closed state by a closure, wherein the closure comprises a lever provided with a slot which for closing can be placed on an eye fastened to the container or the lid such that the eye protrudes from the lever after the closing process and an adhesive indicator strip can be passed through it.

From DE 90 07 070 U1, a seal for securing a closure of a sterilization container is known, consisting of a label and a connecting element having two ends that can be undetachably connected to the label.

It is a disadvantage of known closures and sterilization containers that a seal can be removed without opening the closure and perhaps be replaced by a new seal. This is why sterility is not ensured even with a sealed container. Furthermore, it may happen during usual handling of a sterilization container that a closure is unintentionally opened or a seal is removed by mistake. In the case of a closed container that has no seal, it cannot be retraced whether the container has already been opened and sterility is questionable or if only the seal has been removed, but the container has not been opened. Another disadvantage is that during opening a sealed container a user has to carry out two handling procedures, i.e. removing the seal and opening the closure.

SUMMARY

Starting from the previously described prior art, the invention is based on the object to provide a closure for a medical sterile container as well as a sterile container that can be reliably closed, represents a dependable safeguarding against unintentional or unauthorized opening and allows to draw conclusions regarding the circumstance whether the container has been opened or not, so that the sterility of the sterile container and of the objects received therein is guaranteed until the moment of opening the sterile container.

According to the present invention, this object is achieved by a closure for a medical sterile container comprising a trough-like first container part and a lid-type second container part, in particular for a sterile container for medical instruments and the like comprising a trough-shaped lower container part having a container bottom and a container wall as well as a container lid for arranging on the container wall and for closing the lower container part, comprising a closure flap which can be arranged on one of the container parts so as to be able to pivot between a closed position, in which the container parts are interlocked with each other by means of the closure, and an open position in which the container parts are unlocked, the closure comprising a latch element which in the closed position of the closure interlocks the closure flap with the other container part. The latch element locking the closure in the closed position does not allow to open the closure by mistake.

According to the invention, the latch element is movably arranged on the closure flap, in particular in a linearly movable or rotationally movable manner. The latch element can be moved in particular between its position locking the closure and a position releasing the closure. The latch element can be preferably positioned relative to the closure flap between a locked position, in which the latch element is interlocked with the other container part, in particular with the lower container part, preferably its container wall or a carrier plate arranged thereon, and a release position in which the latch element is unlocked from the other container part. For the purpose of opening the closure, an intentional actuation of the latch element by a user is required, so that the latch element and hence the closure can be unlocked and the closure be opened.

In an advantageous embodiment of the invention, the latch element is arranged on the closure flap in a rotatably movable manner. In particular, the latch element may be formed with a U-shaped design and may have its respective ends provided with lock portions which can be caused to laterally engage an engaging section of the other container part. Further, a connection portion of the two lock portions may be formed to be elastic and each lock portion may be rotatably coupled to the closure flap. This has the advantage that there may be a double-sided engagement of the latch element in the closure flap. The safety against unintentional opening can be enhanced in this way.

In one embodiment, the latch element may be biased into the locked position, in particular by means of a spring. The preload prevents the latch element from being unintentionally unlocked. Any actuation for unlocking has to occur intentionally against the preload force.

In one embodiment, the latch element may have a locking pawl or latching structure which is latched with the other container part in the closed position of the closure, in particular is latched with the other container part if the latch element is in the locked position. A locking pawl is to be seen as an element or a unit which engages behind a suitably shaped mating structure on the other container part or engages it and prevents the closure from moving out of the closed position. The locking pawl retains the closure in the closed position in a reliable manner.

It is especially advantageous if the closure flap comprises a recess and the latch element comprises a recess, with the option that—with the latch element being in the locked position—a seal, in particular a seal such as described in DE 10 2012 004 961 A1 can be arranged in the recesses for sealing the medical sterile container. It is particularly advantageous if the seal in the mounted state is embedded in the recess of the latch element and is flush therewith. As an alternative or in addition, a seal can be arranged on and fastened to the sterile container and in the recesses only if the closure is in the closed position, i.e. in case the sterile container is closed by means of the closure. In particular, fastening and arranging a seal on the sterile container and in the recesses may be impossible if the closure is not correctly closed, in particular if the latch element is not in the locked position. Stated in other words, the sterile container can only be sealed if the closure is correctly closed and if the latch element is in the locked position. If the sterile container has been sealed once, the seal used for that purpose is received in the recesses in such a way that it is not accessible for handling, in particular for opening. It is preferred that the seal can only be opened or removed by a user-side actuation of the latch element, actually by a user-side displacing of the latch element from the locked position to the release position. In other words, the seal is inevitably destroyed during or by opening the closure. This ensures, on the one hand, that a sterile container provided with an undestroyed seal has not been opened after sealing with absolute certainty. On the other hand, it is ensured that a sterile container whose seal is destroyed has been opened with high probability and has been at least unlocked with absolute certainty.

Further, it is of advantage if the latch element, in particular the locking pawl, comprises a contact ramp via which the latch element can be moved out of the locked position during closing the container. In particular in case the latch element is preloaded into its locked position, such process of closing the closure is particularly easy, in fact by simply transferring the closure into its closed position. As soon as the contact ramp reaches the mating structure provided on the container part and intended for locking, the latch element is forced from its locked position toward the release position with a continued closing movement against the preload until it has reached the locked position. At the latest in that stage, the contact ramp is released and the latch element springs back into the locked position due to its preload and locks the closure in the closed position.

In one embodiment, a closure lug may be pivotally arranged on the closure flap in the manner of a toggle lever. The closure lug is preferably designed so as to engage the other container part in the closed position of the closure. A closure of this type allows in an advantageous way relatively high closing forces with relative small actuation forces, so that a tight closing of the container can be achieved in an easy manner, in particular if it comprises an elastic gasket between the lower container part and the lid. In the closed position of the closure, the closure lug may rest against the closure flap. This also allows a flush integration of the closure on the container, being advantageous for transporting and storing the container. In an open position of the closure, the closure lug may be turned away from the closure flap. This allows to make the closure lug engage a dedicated mating structure on the container part and to transfer the closure into the closed position in a particularly easy manner.

In an especially advantageous way, the latch element may encompass the closure flap and the closure lug in the closed position of the closure at least in sections and fix them in position relative to each other. This means that a movement of the closure is not possible without a previous transfer of the latch element from its locked position into the release position, involving an additional safeguard and hence safety regarding the above-mentioned process of locking the latch element to the corresponding container part.

In a further embodiment, the closure lug is biased into a position turned away from the closure flap, in particular by means of a spring. This ensures that the closure lug during the process of closing the container by a user can be correctly positioned relative to the container and made to engage the corresponding mating structure on the container part in a particularly easy and user-friendly way.

In one embodiment, the closure lug may comprise a stop which rests against the closure flap in the state when fully swiveled away from the closure flap. This ensures that the closure lug is always in the same position when the closure is open, further enhancing the manageability of the closure.

In one embodiment, the closure, in particular the spring, may comprise a latching structure, in particular a slot. Said latching structure may be used in particular for being latched with a mating latching structure arranged on the one container part, in particular in a position of the closure fully folded inwards, lying flat on the container part, which offers a special advantage for instance during cleaning and washing procedures. By way of example, the closure may be pivotally arranged on the container lid and the mating latching structure may be arranged or formed on the inner side of the lid. For washing, in particular in a dishwasher or washing machine, the closure can be folded inward so as to rest against the inner side of the lid, while the latching structure comes to engage the mating latching structure and holds the closure in this cleaning position. This improves the manageability of the closure or the sterile container during cleaning in an advantageous way.

The closure flap may have a stop which—when the closure is in the open position—comes to rest against the container part on which the closure flap is arranged. The stop makes contact preferably if the closure, in particular the closure flap, is turned away or protrudes by an angle of approximately 90°. In that case, a user may make use of the closure in an advantageous way as a handle to manipulate the container part on which the closure flap is arranged.

The container may comprise a venting valve for venting a container interior surrounded by the lower container part and the container lid. The venting valve may be coupled to the closure and may be closed in its closed position and open in its open position. The venting valve may be arranged in particular underneath the closure, in particular underneath the closure lug. In that case, it is not accessible for a user and cannot be manipulated, ensuring sterility as long as the sterile container has not been opened. Moreover, the venting valve is hidden behind the closed closure device/closure lug and is not visible, representing a further protection against manipulation.

It is a special advantage if the closure lug situated in its closed position is in engagement with the valve body, in particular with the valve body head, and pushes the valve body into the closed valve position. This results in a direct actuation of the venting valve depending on the respective functional position of the closure device or closure lug.

It is a special advantage if the latching device—with the closure lug being in the closed position—is in engagement with the valve body, in particular with the valve body head, and pushes the valve body into the closed valve position. Here, the venting valve is directly actuated by the latching device. Provision may also be made that the latching device is in engagement with the valve body, in particular with the valve body head, and urges the latter into the closed valve position if the latching device is situated in the position in which the closure lug is locked.

Furthermore, it is advantageous that the venting valve can be automatically closed during closing the sterile container with the container lid, so that a separate manipulation on the venting valve after closing the container is not required, in order to guarantee for tightness and hence sterility. If the container lid is placed on the lower container part and the closure is closed, the valve is automatically or inevitably actuated by the closure device or closure lug and is transferred against its preload to the closed state in which it seals off the through-hole. If the closure latches in place on the corresponding mating latching structure, the venting valve is closed. If the closure is opened again, the venting valve opens automatically into the open position due to its preload.

Linking the venting valve function and the function of the closure device results in a safety venting valve which has a venting effect only if the sterile container is willfully opened. Any unintentional opening or actuating the valve is prevented, and the sterility of the container is ensured until the lid is opened.

A closure according to the invention may further comprise a lug-shaped container attachment, in particular lid attachment, by means of which the closure is to arrange and/or attach to the container or lid. It is preferred that the closure flap can be pivoted relative to the container attachment lug, in particular around a shaft arranged between the closure flap and the container attachment lug.

The object initially mentioned is also achieved by a medical sterile container comprising a closure in one of the previously described embodiments.

Stated in other words, the invention relates to a closure according to the toggle lever principle in a special embodiment. It may be fixed to the container lid via a lid attachment (or cover lug) and pivotally connected to it via a shaft. The closure essentially comprises the closure flap, the closure shaft, the closure lug shaft, the closure lug, compression springs for biasing the latch element, the latch element itself and the closure spring. The closure flap houses both shafts as well as the latch element inclusive of the two compression springs. The closure flap is connected to the lid attachment via the closure shaft. The folding shaft connects the closure snap-lock to the closure lug. The latch element houses the two compression springs and is put onto the closure flap. The closure spring is mounted between the closure flap and the closure snap-lock via the closure shaft. The closure can transfer forces via the lid attachment, the closure shaft, the closure flap, the closure lug shaft and the closure lug to the container wall, in particular to a container faceplate. The latch element engages in the container wall, in particular in a carrier plate arranged thereon, but does not transfer any forces.

In order to ensure that the closure lug is always in the correct position ("unfolded" relative to the closure flap) and hence to guarantee that it engages in the container wall/faceplate always in the correct position, it is pushed into the correct position by the closure spring. If the closure is being closed, the closure spring is compressed. If the closure is opened again, the closure spring pushes the closure lug immediately back toward the initial position. In terms of geometry, the closure lug may be shaped here such that it constitutes a stop for the closure flap and thus always "deflects" into the correct position.

If the closure is open, it can be used as a holding element, in particular as a holding element on the lid. To this end, the closure is opened and moved to a position which is horizontal relative to the lid. The closure comprises a geometrically shaped stop with which the closure flap strikes against the lid attachment. The closure thus forms a fixed holding element which ensures that the lid can be lifted in a safe manner.

For washing or cleaning, the closure can be folded "inwards" to be horizontal relative to the lid and latch in place in this position. To this end, the closure spring latches in place in the cover lug. Its upper area may be formed with a slot for that purpose. The cover lug may comprise a mating component in the form of two detents behind which the closure spring snaps in place. For latching the closure, it will be opened and the slotted closure spring slides over the detents into the latching position, while the spring ends are bent toward the middle. A form-fit between the closure spring and the cover lug allows to hold the closure in the horizontal position relative to the lid. If the closure is removed from the latching position, the closure spring can be pulled out of the latched state in the same way.

If the closure is being closed, the closure catch snaps in place in the container wall or faceplate and "travels/slides" therein from the folded state to the closed state. To this end, the closure is designed such that the closure lug upon closing the closure deflects so as to approach the closure flap and changes the "angle" relative to the container wall/faceplate. In this process, a position of the closure lug parallel to the closure flap is passed. Having passed said parallel position, the closure fully snaps in place in an independent way.

The closure may be arrested by the latch element in the closed state. To this end, the latch element is latched in place in the container wall, in particular in a carrier plate arranged thereon. For being latched, the closure may be simply closed by a user or, in other words, pressed shut. An inclined plane helps to press the closure "upwards" until it is able to engage the container wall or the carrier plate. The compression springs inserted in the latch element and supported in the closure flap allow to immediately press the latch element "downwards" after having engaged the cut-out of the carrier plate. The closure is arrested by the geometrical undercut of the latch element.

As a protection against unintended opening, it may be required to actively actuate the latch element for opening the closure, in order to disengage its latching in the container wall/carrier plate. To this end, the closure latching can be pushed "upwards" by the user. As a second safeguard against unintended opening, it may be required to actively release the closure (which is unlocked now) from the latched state. Provision may be made that merely opening the closure locking is not sufficient for opening the closure.

The closure may be designed such that it is capable of receiving the seal in the closed and locked state. To this end, the closure flap may have an opening for inserting the seal therethrough. Provision may be made that sealing a container which has not been correctly closed is impossible. If the closure is not closed or if the latch element is not correctly latched with the lower container part, the closure protrudes from the lower container part so far that the inserted seal cannot be sealed. If the seal is attached prior to closing the closure, the closure cannot be closed any more. In case the closure is closed and secured with a seal, the closure can only be opened by destroying the seal. To this end, the closure can be unlocked and opened by actuating the latch element. During the opening procedure, the closure flap can engage the latched seal and destroy it by bending open the seal wings in a destructive manner. The closure may also be designed such that a removal of the attached seal is exclusively possible in a destructive manner. If the seal has been mounted, it may be embedded in a recess of the latch element and be flush therewith. Any turning movement of the seal, as required for removing it, may be impossible due to geometric reasons.

BRIEF DESCRIPTION OF THE DRAWING FIGURES

Further features and advantages of the present invention will be apparent from the following exemplary description of the invention and a particularly preferred embodiment with the aid of Figures which are only of schematic nature and merely serve the purpose of understanding the invention. In the Figures.

DETAILED DESCRIPTION

Figure 1:
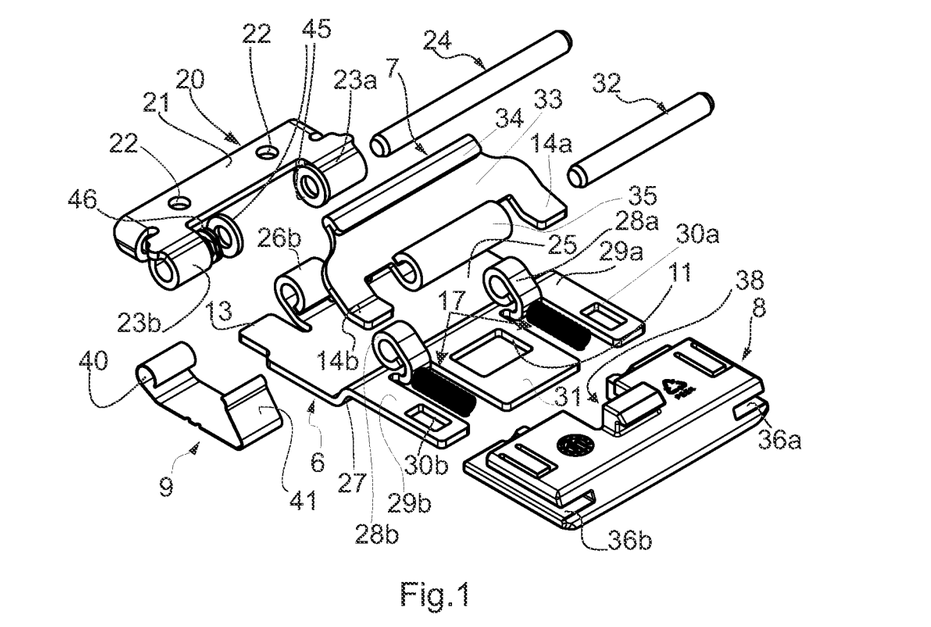
FIG. 1 shows a closure for a medical sterile container according to a first embodiment of the invention in a perspective exploded view.

FIG. 1 shows a closure for a medical sterile container 1 according to the invention in a perspective exploded view. In the sectional views of FIGS. 5 to 8, the closure is illustrated in sectional views in which parts of the sterile container 1 can be seen. Said sterile container comprises a lower container part 2 and a lid 5 as container parts. The lower container part 2 comprises a container bottom 3 and a container wall 4. The container lid 5 is to be arranged or is arranged on the side of the container wall 4 facing away from the container bottom 3. The container lid 5 is sealed off with respect to the container wall 4 with a gasket 18, so that in the closed state of the sterile container 1 the interior 19 of the latter is hermetically sealed with respect to the surrounding, with the exception of possibly provided filters and filter openings which, however, are not shown in the Figures.

Arranged on the container lid 5 is a cover lug 20, in particular by means of rivets or screws. The cover lug 20 is a molded sheet metal part and is illustrated in a perspective view in FIG. 1. It comprises essentially a base plate 21 which has two holes 22 formed therein for receiving fastening screws or fastening rivets. In the state when fastened to the lid 5, the lower side of the base plate 21 comprises two lugs which are formed as a left bearing seat 23a and a right bearing seat 23b. The bearing seats 23a,b serve for receiving a closure shaft 24 which is formed from a cylindrical axle pin.

By means of the closure shaft 24, a closure flap 6 is arranged on the cover lug 20 and hence on the lid 5 so as to be able to pivot around the shaft 24. The closure flap 6 is implemented as a molded sheet metal part as well. It essentially consists of an elongated, z-shaped base plate 25 at one end side of which two lugs are formed as a left bearing seat 26a and a right bearing seat 26b. Laterally beyond the bearing seats 26a,b, there is formed a stop 13 in each case by end-side protrusions of the base plate 25. These stops 13 rest against the cover lug 20 when the closure is completely turned away from the lid 5 and define a maximum swing angle α by which the closure flap 6 can be turned away relative to the plane of the lid 5.

Between the bearing seats 23a,b of the cover lug 20 and the bearing seats 26a,b of the closure flap 6, the shaft 24 is provided with one Teflon disk 45 in each case. A multi-corrugated spring washer 46 is additionally provided on one bearing seat side (in FIG. 1 the left one) between the left bearing seat 23a and the corresponding Teflon disk 45. The multi-corrugated spring washer 46 exerts an axial force between the two bearing seats 23a, 26a and establishes via the Teflon disks 45 a mechanical escapement between the cover lug 20 and the closure flap 6 and between the lid 5 and the closure. This achieves a permanent "sluggishness" of the closure. The closure is prevented from any "flapping". Due to the escapement, the closure is "foldable" for cleaning purposes. Thus, the weight force of the closure is supported. The use of the multi-corrugated spring washer 46 as well as of the Teflon disk 45 provides a wear-free kind of escapement. Known solutions such as conical shafts, curved shafts, crossed bearing seats as well as the technique to press the shaft into the bearing seat at one side entail high friction and loose their escapement throughout the service life. As an alternative, a disk made of stainless steel or plastic may also be used instead of a Teflon disk 45.

A step 27 is provided approximately in the middle of the closure flap 6. On the side of the step 27 opposite to the bearing seats 26a,b, two strips parallel to each other are cut out from the base plate 25 and are bent such that they form two bearing seats 28a,b. The bearing seats 28a,b and the bearing seats 26a,b are arranged on one and the same side of the base plate 25. The free spaces produced by bending the strips for the bearing seats 28a,b each accommodate a spring 17, here a spiral spring 17. Laterally beyond the free spaces accommodating the springs 17, the base plate 25 is formed so as to have side lugs 29a,b. Each side lug 29a,b is provided with a recess 30a and 30b, respectively. As will be explained in more detail below, the recesses 30a,b serve for realizing an assembly which can be moved toward the base plate 25 and for holding a latch element 8. Between the bearing seats 28a,b, the base plate 25 is formed as a center lug 31. Said center lug has a middle recess 11 serving for receiving a seal 12 for sealing the sterile container 1. The seal 12 can be seen in FIGS. 5 and 6 and is described in detail in DE 10 2012 004 961 A1.

A closure lug 7 is pivotally arranged on the closure flap 6 by means of the bearing seats 28a,b. To this end, a closure lug shaft 32 formed from a cylindrical axle pin is received in the bearing seats 28a,b. The closure lug 7 is realized as a sheet metal part. It comprises essentially a base plate 33 which has its end side bent so as to form a reinforced engaging tongue 34. At its end opposite the engaging tongue 34, the closure lug 7 is bent in a middle section so as to form a bearing shaft seat 35. The bearing shaft seat 35, the closure lug shaft 32 and the bearing seats 28a,b form a swivel bearing by means of which the closure lug 7 is pivotally arranged on the closure flap 6. Laterally beyond the bearing shaft seat 35, the closure lug 7 comprises two stops 14a,b which delimit a swing angle β between the closure lug 7 and the closure flap 6. In combination with the pivot shafts 24 and 32, the closure flap 6 and the closure lug 7 form a toggle lever mechanism.

Figure 2:
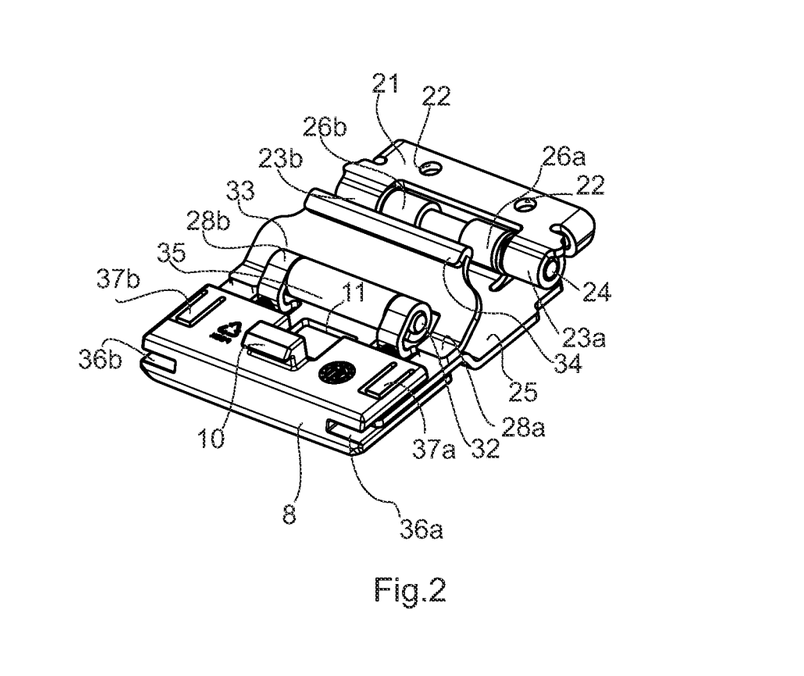
FIG. 2 shows the closure of FIG. 1 in the mounted state in a schematic perspective illustration.
Figure 3:
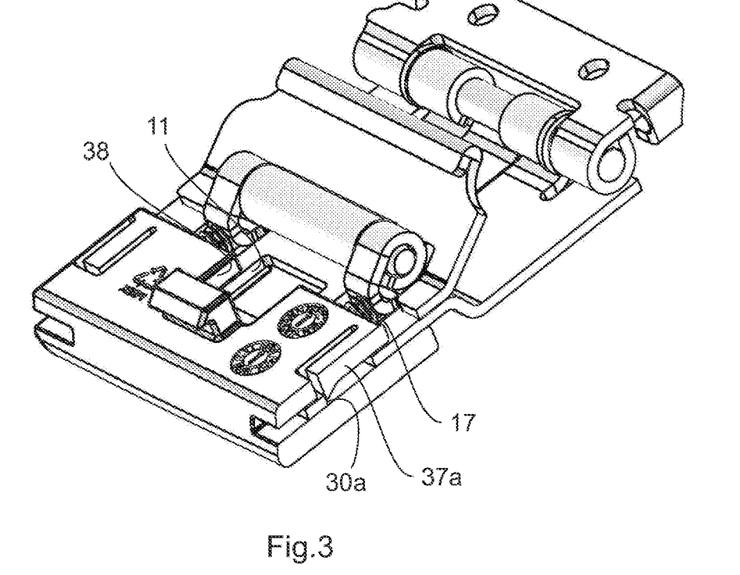
FIG. 3 is a partial sectional view of FIG. 2.
Figure 4:
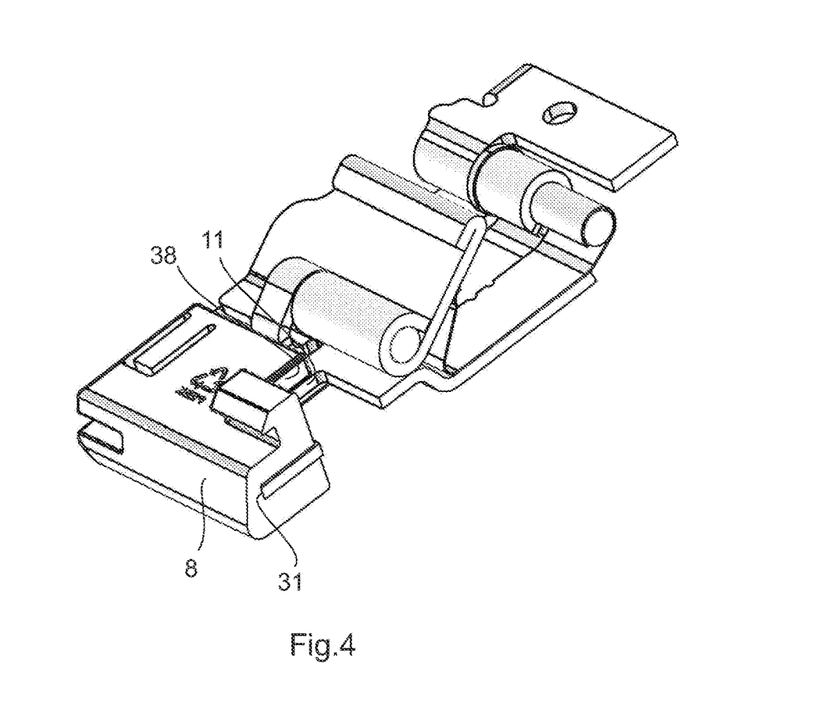
FIG. 4 is a further partial sectional view of FIG. 2.

The closure further comprises the latch element 8. The latter is designed as an injection-molded part in the illustrated embodiment. The latch element 8 comprises two lateral recesses 36a,b extending in the longitudinal direction of the closure which serve for receiving the two side lugs 29a,b of the closure flap 6. Arranged in the area of each slot-shaped recess 36a,b is a spring element (spring tongue) 37a,b which engages the respective recess 30a,b of the corresponding side lug 29a,b (see FIG. 2 and FIG. 3). The latch element 8 can be moved with respect to the closure flap 6 in the longitudinal direction of the closure. Here, the spring elements 37a,b engaging the recesses 30a,b form a first, lower stop in the open position of the closure, i.e. if the closure is not locked in place in the lower container part 2 or the carrier plate, against which the latch element 8 is pressed in a spring-loaded manner (spring 17) and which defines an end position of the latch element 8 on the closure flap 6 (see FIG. 3). The movement of the latch element 8 in the opposite direction, i.e. contrary to the spring forces of the spring 17, is delimited by a second, upper stop which is formed by a middle section of the latch element 8 and hit by a front edge of the center lug 31 (see FIG. 4).

For the purpose of locking the closure on the sterile container 1, the latch element 8 comprises a locking pawl 10 which can get caught with a latching edge 39 of the lower container part 2. In the closed position of the closure, i.e. if the closure is locked in place in the lower container part 2, the lower stop is not formed by the spring elements 37a,b, but by the locking pawl 10 which strikes against the latching edge 39 of the lower container part 2 in the closed position of the closure (see FIG. 5).

Figure 5:
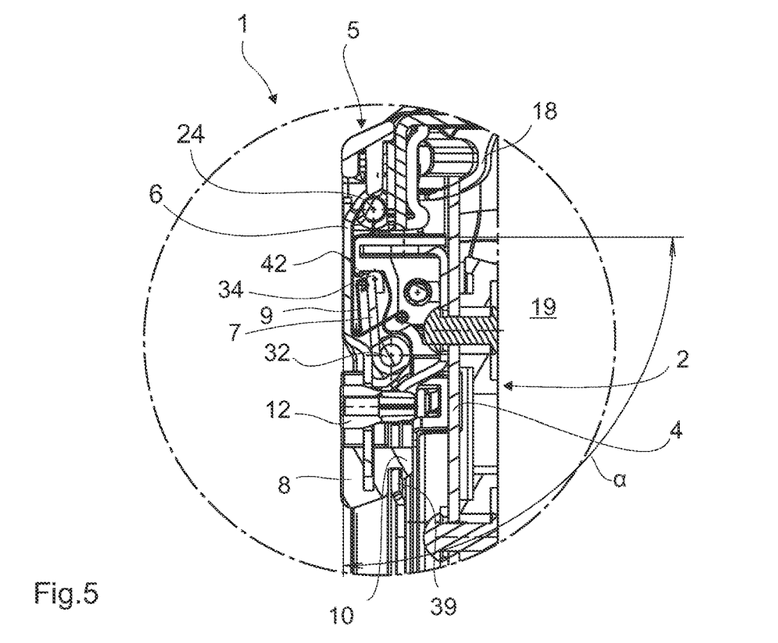
FIG. 5 shows a closure according to the invention, arranged on a sterile container, as seen in a sectional view and in the closed position.

If the locking pawl rests against the latching edge 39 of the lower container part 2, the latch element 8 is in a locked position in which it is able to lock the closure with respect to the sterile container 1 in its closed position. If the middle section of the latch element 8 rests against the front edge of the center lug 31 of the closure flap 6, the latch element 8 is in a release position where it is spaced from the cover lug 20 with minimum distance and is capable of unlocking the closure with respect to the sterile container 1 from its closed position.

The latch element 8 comprises a middle recess 38. Regarding its size and position, said recess is adjusted to the recess 11 provided in the closure flap 6 such that the recess 11 in the closure flap 6 is not covered by the latch element 8, neither if the latch element 8 is in the locked position nor if the latch element 8 is in the release position (see FIG. 3 and FIG. 4).

A seal 12 can be arranged in the latch element 8 if the latter is in the locked position. This is not possible if the latch element 8 has been moved out of the locked position. If a seal 12 is arranged in the recesses 11 and 38 and the sterile container 1 is sealed with these, the seal is housed by the closure, in particular by the latch element 8 in such a way that it is not accessible by a user and cannot be removed without displacing the latch element 8 and opening the closure. Furthermore, the seal 12 is inevitably destroyed by opening the closure, as the closure flap 6 engages the locked seal and bends up the seal wings in a destructive manner.

The closure flap 6 and the closure lug 7 are prestressed against each other by means of a closure spring 9. The closure spring 9 is a bent part or molded sheet metal part made of spring steel and its end side is bent so as to form a bearing shaft seat 40. It is arranged on the closure shaft 24 by means of said bearing shaft seat. At its side opposite the bearing shaft seat 40, the closure spring is bent by more than 90° and forms a spring arm 41. The closure spring 9 rests against the closure flap 6 at the side of the closure lug 7 by means of the section situated between the bearing shaft seat 40 and the spring arm 41 and is arranged between said closure flap and the closure lug 7. The spring arm 41 is supported by the closure lug 7, so that the closure spring 9 biases the closure lug 7 into a position turned away from the closure flap 6. The closure lug 7 can be pivoted toward the closure flap 6 against the preload of the closure spring 9.

FIGS. 5 to 8 show the closure in sectional views in different positions relative to the sterile container 1, in order to clarify the way of functioning of the closure. FIG. 5 shows the closure with the closure flap 6 in the closed position. The closure flap 6 rests laterally against the container wall 4. The engaging tongue 34 engages behind a latching edge 42 of the lower container part 2, so that the lid 5 is pulled toward the container wall 4 and rests against the gasket 18 in a tight manner. The locking pawl 10 of the latch element 8 engages behind the latching edge 39 in the closed position. The latch element 8 is in the locked position. The seal 12 reaches through the two recesses 11 and 38 and is received therein so as to be not accessible for a user.

Figure 6:
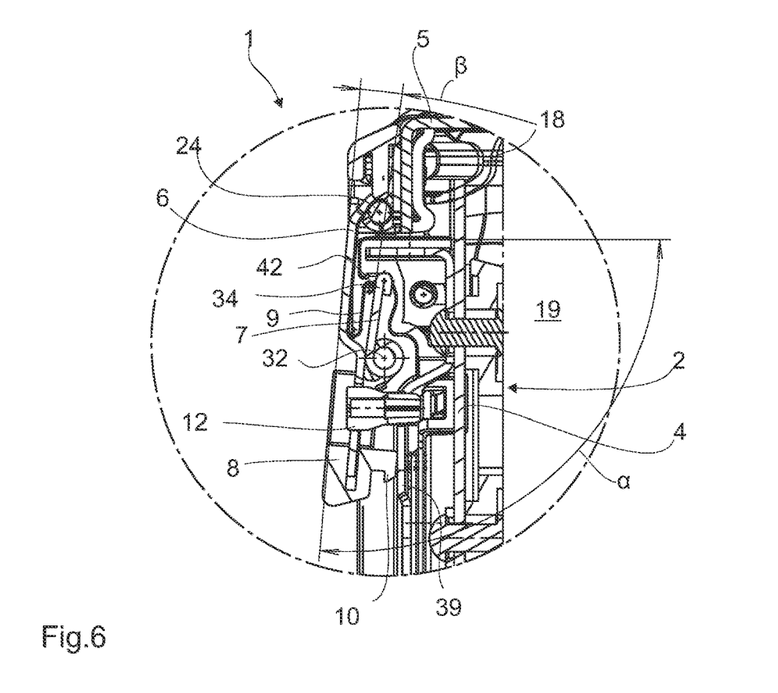
FIG. 6 shows the closure of FIG. 5 in a position which is opened by an angle of 3° with respect to the closed position.

For opening the closure, a user has to displace the latch element 8 against the preload of the compression springs 17 toward the cover lug 20 (in FIG. 5 upwards). The locking pawl 10 is released from the latching edge 39 and the closure flap can be turned away from the container wall 4 around the closure shaft 24. In doing so, the seal situated in the recesses 11, 38 is destroyed. Due to the toggle lever-like design of the closure, the closure lug 7 swivels away from the closure flap 6. FIG. 6 shows the closure shortly before destroying the seal 12.

Figure 7:
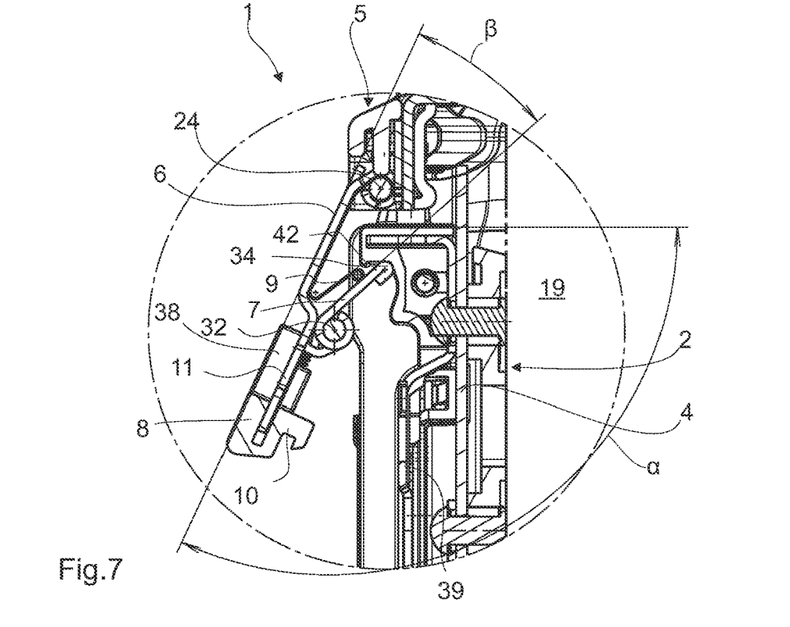
FIG. 7 shows the closure of FIG. 5 in a position which is opened by an angle of 23° with respect to the closed position.
Figure 8:
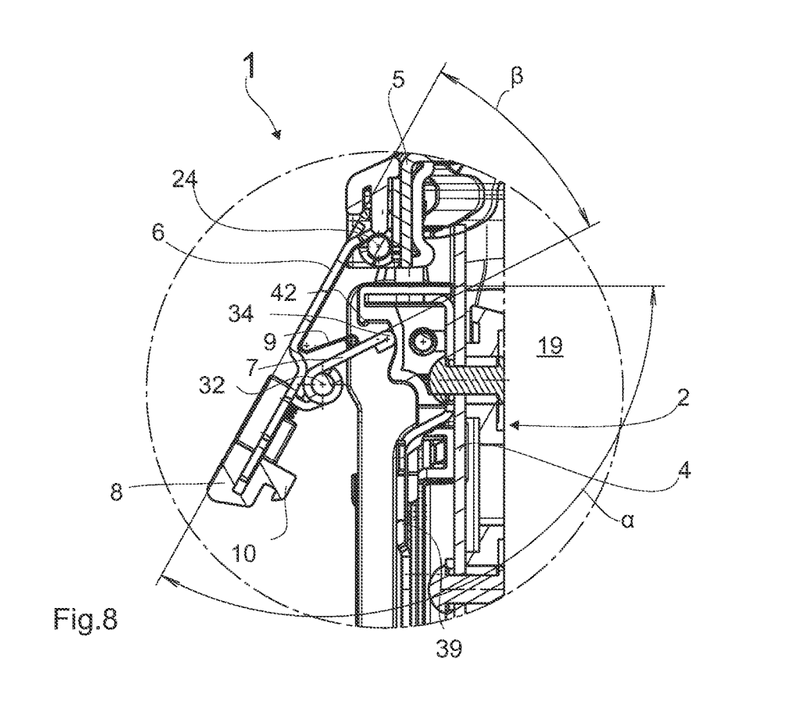
FIG. 8 shows the closure of FIG. 5 in a position which is opened by an angle of 34° with respect to the closed position.

FIG. 7 shows the closure in a position where it is turned away farther from the container wall 4 than in FIG. 6. The engaging tongue 34 still makes contact behind the latching edge 42. The seal 12 is destroyed and removed. Comparing FIGS. 6 and 7, it can be clearly seen how the closure spring 9 is unstressed with an increasing swing angle α. FIG. 8 finally shows the closure in a position in which the engaging tongue 34 has come loose from the lower container part 2. It can be taken in particular from FIG. 7 that a seal cannot be fastened and sealed if the closure—although in engagement on the lower container part 2 and the lid 5—is not yet fully closed (FIG. 5). The process of sealing is only possible in the position of FIG. 5.

A second embodiment of a closure, according to the invention, for a medical sterile container is explained on the basis of FIGS. 9 to 12; in the following, only the differences to the first embodiment will be elucidated and regarding identical features and functions reference is made to the description of the previous specification of the first embodiment.

Figure 9:
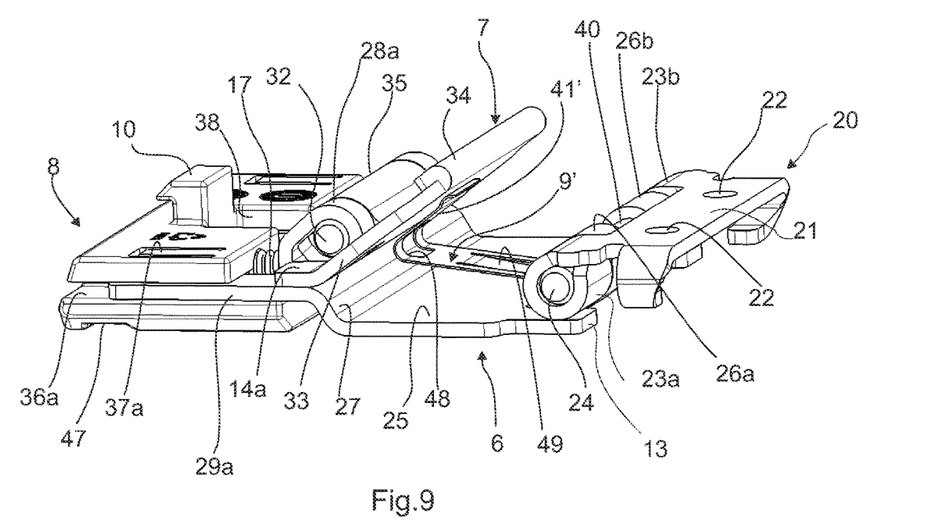
FIG. 9 shows a closure for a medical sterile container according to a second embodiment of the invention in a schematic perspective illustration.
Figure 10:
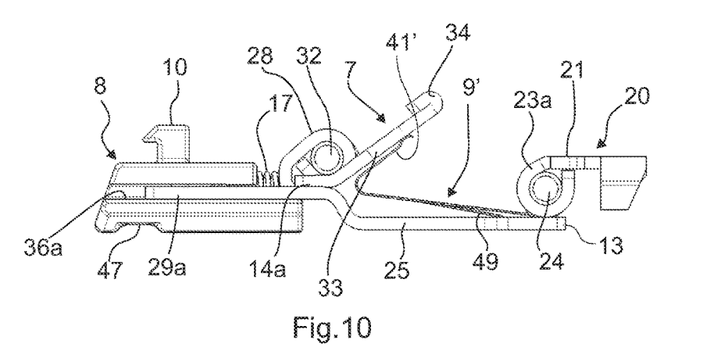
FIG. 10 shows the closure of FIG. 9 in a side view.

The second embodiment differs from the first embodiment essentially only in the design of the latch element 8' and the closure spring 9'.

The latch element 8' additionally comprises—at its outer side or the side facing away from the container in the mounted state—a transverse groove 47 which is horizontal or extends parallel to the shafts 24 and 32 and facilitates the handling of the latch element 8' during displacing it relative to the closure flap 6 against the spring force of the springs 17.

The spring arm 41' of the closure spring 9' supported by the closure lug 7 has a middle recess 48. The section of the closure spring situated between the bearing shaft seat 40 and the spring arm 41' comprises a spring tongue 49 which rests against the surface of the base plate 25 of the closure flap 6 in a spring-biased manner (see FIG. 10). Similar to the first embodiment, the spring arm 41' of the closure lug 7 is supported, so that the closure spring 9' biases the closure lug 7 into a position turned away from the closure flap 6. The closure lug 7 can be pivoted toward the closure flap 6 against the preload of the closure spring 9'. In this process, the spring tongue 49 remains in constant contact with the base plate 25.

Figure 11:
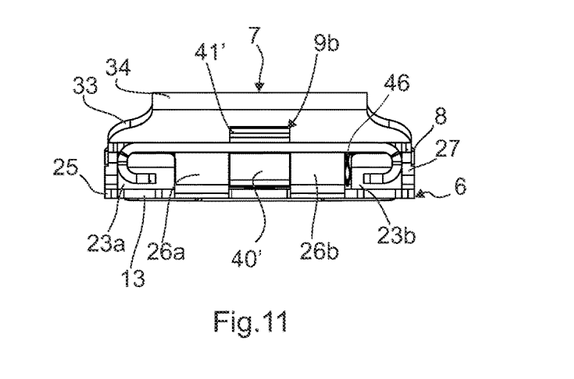
FIG. 11 is an end view of FIG. 9.
Figure 12:
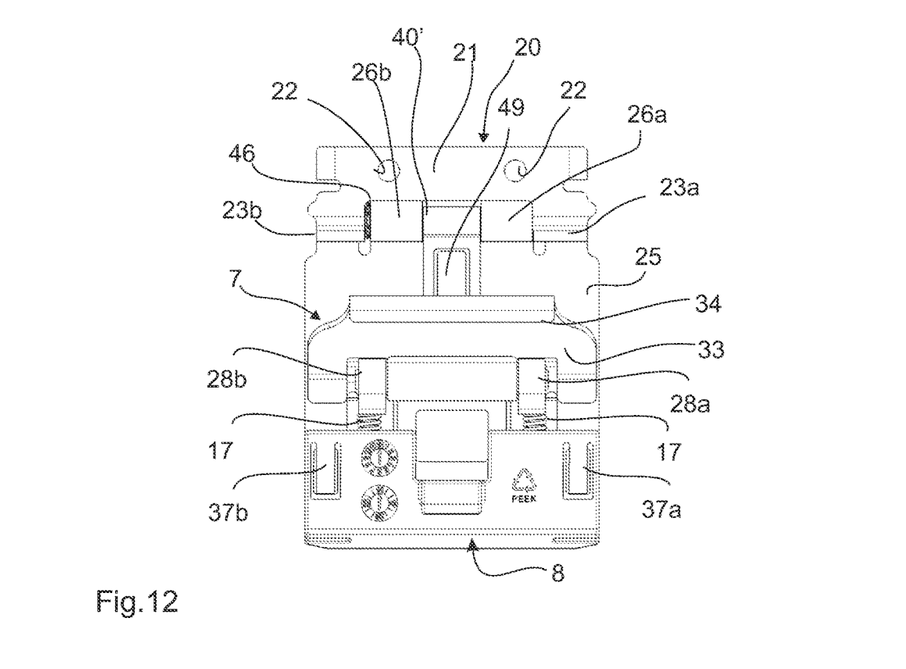
FIG. 12 is a rear view of the closure of FIG. 9.
Figure 13:
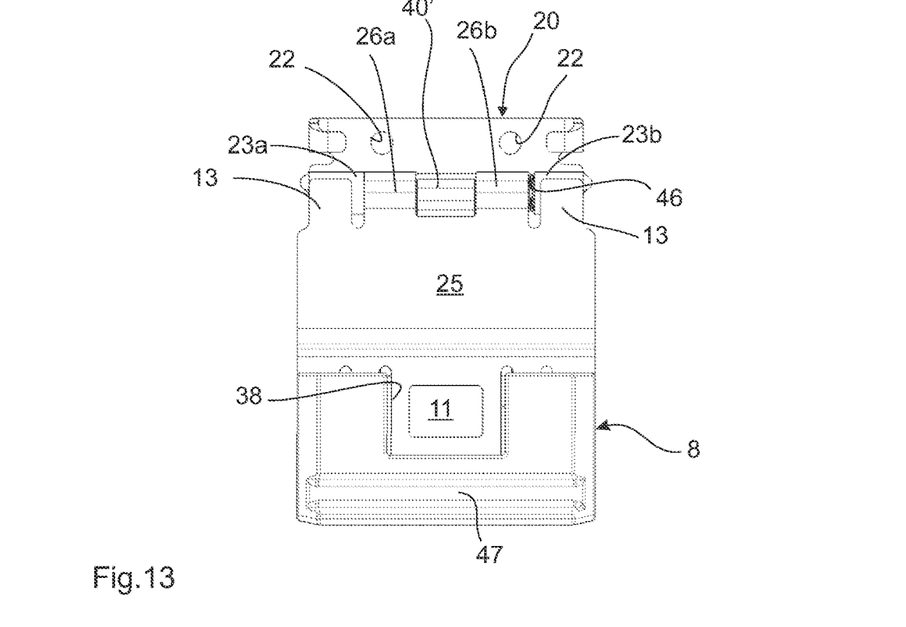
FIG. 13 is a front view of the closure of FIG. 9.

A further difference to the first embodiment can be taken from FIGS. 11 and 12. In the second embodiment, there are no Teflon disks 45 between the bearing seats 23a,b of the cover lug 20 and the bearing seats 26a,b of the closure flap 6. On a bearing seat side, the multi-corrugated spring washer 46 is directly interposed between the left bearing seats 23b and 26b in a sandwich-like manner.

In order to further enhance the mechanical escapement and the desired sluggishness of the closure, friction pads may be provided on or between the bearing seats 23a,b and 26a,b.

The spring washer 46 may be designed as an adjustable spring washer in order to be able to adapt the mechanical escapement or desired sluggishness to the respective requirements and to readjust it after prolonged use, if need be.

FIG. 11 shows a rear view, i.e. the side of the closure facing the container, and FIG. 12 shows a front view, i.e. the outer side or the side of the closure facing the user.

In other respects, the way of functioning and the effect of the second embodiment correspond to those of the first embodiment.

Figure 14:
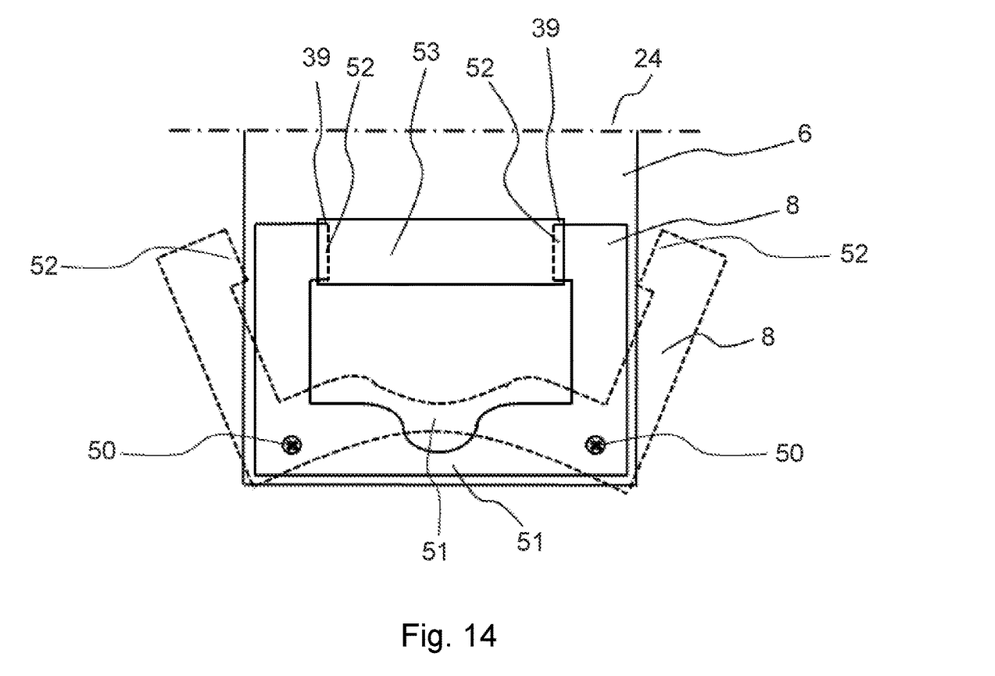
FIG. 14 shows the closure for a medical sterile container according to a third embodiment of the invention in a schematic illustration.

FIG. 14 shows a closure for a medical sterile container according to a third embodiment of the invention in a schematic illustration. Here, the latch element 8 is rotatably movably arranged on the closure flap 6. The latch element 8 and the closure flap 6 are provided on a (not illustrated) first container part so as to be able to pivot around the closure shaft 24. The latch element 8 is illustrated in FIG. 14 in a disengaged state swiveled towards outside as well as in an engaged, meshing state. In the engaged state, locking protrusions 52 provided on the latch element 8 engage latching edges 39 of an engaging section 53 of a (not illustrated) second container part. The locking protrusions 52 may have in particular inclined ramp surfaces. In a locked state of the lock bar, an undercut is preferably formed between the locking protrusions 52 and the engaging section 53. The latch element 8 can be rotated or swiveled outwards and inwards relative to the closure shaft around two pivot points 50, namely a right-hand pivot point 50 and a left-hand pivot point 50. In a middle section between the pivot point 50, an elastic section 51 of the latch element 8 is provided which is extended when the latch element 8 is pivoted in outward direction and changes into its non-extended original state again when the latch element 8 is pivoted inwards. Instead of the fixed pivot points 50, it is also possible to provide elongated holes on the sides, and instead of the elastic section 51 a joint in the middle area of the latch element 8 may be provided.

The invention claimed is:

1. A closure for a medical sterile container comprising a first container part and a second container part, the closure comprising:
    a closure flap which is arranged on one of the first container part and second container part so as to be able to pivot between a closed position, in which the first and second container parts are interlocked with each other by means of the closure, and an open position in which the first and second container parts are unlocked
    a closure lug that is pivotally arranged as a toggle lever on the closure flap, the closure lug designed to engage the other of the first container part and second container part in the closed position of the closure; and
    a latch element which in the closed position of the closure interlocks the closure flap with the other of the first container part and second container part, the latch element being movably arranged on the closure flap between a position locking the closure and a position releasing the closure; wherein the latch element comprises a locking pawl which in the closed position of the closure with the latch element being in the locked position is locked in place on the other of the first container part and second container part.

2. The closure for a medical sterile container according to claim 1, wherein the latch element is arranged on the closure flap so as to be able to be linearly moved.

3. The closure for a medical sterile container according to claim 1 wherein the latch element can be positioned relative to the closure flap between a locked position, in which the latch element is interlocked with the other container part, and a release position in which the latch element is unlocked from the other of the first container part and second container part.

4. The closure for a medical sterile container according to claim 1, wherein the closure flap comprises a recess and the latch element comprises a recess, a seal for sealing the medical sterile container being able to be disposed in the recesses of the closure flap and latch element when the latch element is in the locked position.

5. The closure for a medical sterile container according to claim 1, wherein the seal when mounted is embedded in and flush with the recess of the latch element.

6. The closure for a medical sterile container according to claim 1, wherein the closure lug rests against the closure flap in the closed position of the closure and is swiveled away from the closure flap in an open position of the closure.

7. The closure for a medical sterile container according to claim 6, wherein the closure lug comprises a stop which rests against the closure flap when the closure lug is fully swiveled away from the closure flap.

8. The closure for a medical sterile container according to claim 1, wherein the latch element encompasses the closure lug at least in sections in the closed position of the closure.

9. The closure for a medical sterile container according to claim 1, wherein the latch element is prestressed toward the locked position by a spring.

10. The closure for a medical sterile container according to claim 1, wherein the locking pawl of the latch element comprises a contact ramp via which the latch element is moved out of the locked position during closing of the container.

11. The closure for a medical sterile container according to claim 1, wherein the closure lug is biased into a position turned away from the closure flap by a spring.

12. The closure for a medical sterile container according to claim 1, wherein the latch element is arranged on the closure flap in a rotatably movable manner.

13. A medical sterile container comprising a closure for a medical sterile container comprising a first container part and a second container part, the closure comprising:

A closure flap which is arranged on one of the first container part and second container part so as to be able to pivot between a closed position, in which the first and second container parts are interlocked with each other by means of the closure, and an open position in which the first and second container parts are unlocked;

A closure lug that is pivotally arranged so as to toggle lever on the closure flap, the closure lug designed to engage the other of the first container part and second container part in the closed position of the closure; and A latch element which in the closed position of the closure interlocks the closure flap with the other of the first container part and second container part, the latch element being movably arranged on the closure flap between a position locking the closure and a position releasing the closure;

Wherein the latch element comprises a locking pawl which in the closed position of the closure with the latch element being in the locked position is locked in place on the other of the first container part and second container part.

14. The medical sterile container according to claim 13, wherein the medical sterile container comprises a venting valve for venting a container interior surrounded by the first container part and the second container part, wherein the venting valve is coupled to the closure and is closed in the closed position and open in the open position of the closure.

15. The medical sterile container according to claim 14, wherein the venting valve is arranged underneath the closure lug.

16. The medical sterile container according to claim 14, wherein, when the closure lug is situated in its closed position, the closure lug is in engagement with a valve body head of the venting valve and pushes the venting valve into a closed valve position.

17. The medical sterile container according to claim 13, wherein the closure comprises a geometrically shaped stop with which the closure flap strikes against a lid attachment of one of the first container part and second container part.

* * * * *